United States Patent [19]
Yoon

[11] Patent Number: 5,797,958
[45] Date of Patent: Aug. 25, 1998

[54] ENDOSCOPIC GRASPING INSTRUMENT WITH SCISSORS

[76] Inventor: InBae Yoon, 2101 Highland Ridge Dr., Phoenix, Md. 21131

[21] Appl. No.: 760,245

[22] Filed: Dec. 4, 1996

Related U.S. Application Data

[63] Continuation-in-part of Ser. No. 612,634, Mar. 6, 1996, and Ser. No. 376,186, Jan. 20, 1995, Pat. No. 5,665,100, which is a continuation-in-part of Ser. No. 281,814, Jul. 28, 1994, abandoned, which is a continuation of Ser. No. 73,193, Jun. 8, 1993, Pat. No. 5,334,209, which is a continuation of Ser. No. 720,381, Jun. 25, 1991, Pat. No. 5,217,473, which is a division of Ser. No. 446,555, Dec. 5, 1989, Pat. No. 5,026,379, said Ser. No. 612,634, is a continuation of Ser. No. 281,814.

[51] Int. Cl.$^6$ ...................................... A61B 17/04
[52] U.S. Cl. ...................... 606/207; 606/139; 606/140; 606/170
[58] Field of Search ...................... 606/144–148, 606/139, 170, 157, 158

[56] References Cited

U.S. PATENT DOCUMENTS

| | | |
|---|---|---|
| 2,002,594 | 5/1935 | Wappler et al. . |
| 2,004,559 | 6/1935 | Wappler et al. . |
| 2,011,169 | 8/1935 | Wappler . |
| 2,028,635 | 1/1936 | Wappler . |
| 2,031,682 | 2/1936 | Wappler et al. . |
| 2,032,860 | 3/1936 | Wappler et al. . |
| 2,068,721 | 1/1937 | Wappler et al. . |
| 2,316,297 | 4/1943 | Southerland et al. . |
| 2,518,994 | 8/1950 | Miller . |
| 2,691,370 | 10/1954 | Wallace . |
| 3,827,277 | 8/1974 | Weston . |
| 3,856,016 | 12/1974 | Davis . |
| 3,870,048 | 3/1975 | Yoon . |
| 3,871,379 | 3/1975 | Clarke . |
| 3,911,923 | 10/1975 | Yoon . |
| 3,958,576 | 5/1976 | Komiya . |
| 3,967,625 | 7/1976 | Yoon . |
| 3,980,086 | 9/1976 | Kletschka et al. . |
| 3,989,049 | 11/1976 | Yoon . |
| 4,049,002 | 9/1977 | Kletschka et al. . |
| 4,085,743 | 4/1978 | Yoon . |
| 4,103,680 | 8/1978 | Yoon . |
| 4,174,715 | 11/1979 | Hasson . |
| 4,226,239 | 10/1980 | Polk et al. . |
| 4,249,533 | 2/1981 | Komiya . |
| 4,249,535 | 2/1981 | Komiya . |
| 4,257,420 | 3/1981 | Terayama . |
| 4,274,415 | 6/1981 | Kanamoto et al. . |
| 4,374,523 | 2/1983 | Yoon . |
| 4,393,872 | 7/1983 | Reznik et al. . |
| 4,427,014 | 1/1984 | Bel et al. . |
| 4,471,766 | 9/1984 | Terayama . |
| 4,484,581 | 11/1984 | Martin et al. . |
| 4,493,319 | 1/1985 | Polk et al. . |
| 4,644,951 | 2/1987 | Bays . |
| 4,662,371 | 5/1987 | Whipple et al. . |
| 4,669,470 | 6/1987 | Brandfield . |
| 4,674,501 | 6/1987 | Greenberg . |
| 4,712,545 | 12/1987 | Honkanen . |
| 4,739,760 | 4/1988 | Chin et al. . |
| 4,777,950 | 10/1988 | Kees, Jr. . |

(List continued on next page.)

FOREIGN PATENT DOCUMENTS 2469912  11/1979  France .

*Primary Examiner*—Gary Jackson

[57] ABSTRACT

A multifunctional endoscopic instrument for use in performing endoscopic procedures within an anatomical cavity includes a handle and an elongate tubular member having a proximal end coupled with the handle for being disposed externally of the anatomical cavity and a distal end for being disposed within the anatomical cavity and carrying a pair of opposed, relatively movable jaws. The jaws are operable by manipulation of the handle to grasp objects, such as needles, and to cut tissue. In addition, the elongate tubular member defines a channel permitting fluids and other instruments to be communicated at the operative site without the need of having to remove the endoscopic instrument from the body.

18 Claims, 5 Drawing Sheets

U.S. PATENT DOCUMENTS

| | | |
|---|---|---|
| 4,788,966 | 12/1988 | Yoon . |
| 4,860,746 | 8/1989 | Yoon . |
| 4,869,268 | 9/1989 | Yoon . |
| 4,935,027 | 6/1990 | Yoon . |
| 4,949,717 | 8/1990 | Shaw . |
| 4,961,743 | 10/1990 | Kees, Jr. et al. . |
| 4,985,030 | 1/1991 | Melzer et al. . |
| 4,990,152 | 2/1991 | Yoon . |
| 5,015,249 | 5/1991 | Nakao et al. . |
| 5,026,379 | 6/1991 | Yoon . |
| 5,049,153 | 9/1991 | Nakao et al. . |
| 5,099,827 | 3/1992 | Melzer et al. . |
| 5,100,418 | 3/1992 | Yoon et al. . |
| 5,147,356 | 9/1992 | Bhatta . |
| 5,147,357 | 9/1992 | Rose et al. . |
| 5,147,373 | 9/1992 | Ferzli .......................................... 606/144 |
| 5,152,780 | 10/1992 | Honkanen et al. . |
| 5,156,608 | 10/1992 | Troidl et al. . |
| 5,156,609 | 10/1992 | Nakao et al. . |
| 5,170,800 | 12/1992 | Smith et al. . |
| 5,171,250 | 12/1992 | Yoon . |
| 5,171,258 | 12/1992 | Bales et al. . |
| 5,172,700 | 12/1992 | Bencini et al. . |
| 5,176,695 | 1/1993 | Dulebohn . |
| 5,176,700 | 1/1993 | Brown et al. . |
| 5,192,298 | 3/1993 | Smith et al. . |
| 5,196,023 | 3/1993 | Martin . |
| 5,203,785 | 4/1993 | Slater . |
| 5,211,655 | 5/1993 | Hasson . |
| 5,217,030 | 6/1993 | Yoon . |
| 5,217,460 | 6/1993 | Knoepfler . |
| 5,217,473 | 6/1993 | Yoon . |
| 5,219,354 | 6/1993 | Choudhury et al. . |
| 5,220,928 | 6/1993 | Oddsen et al. . |
| 5,222,961 | 6/1993 | Nakao et al. . |
| 5,222,962 | 6/1993 | Burkhart . |
| 5,222,976 | 6/1993 | Yoon . |
| 5,226,908 | 7/1993 | Yoon . |
| 5,300,087 | 4/1994 | Knoepfler . |
| 5,318,589 | 6/1994 | Lichtman . |
| 5,334,199 | 8/1994 | Yoon . |
| 5,334,209 | 8/1994 | Yoon . |
| 5,342,381 | 8/1994 | Tidemand . |
| 5,342,389 | 8/1994 | Haber et al. . |
| 5,342,390 | 8/1994 | Slater et al. . |
| 5,366,459 | 11/1994 | Yoon . |
| 5,620,459 | 4/1997 | Lichtman ................................. 606/205 |

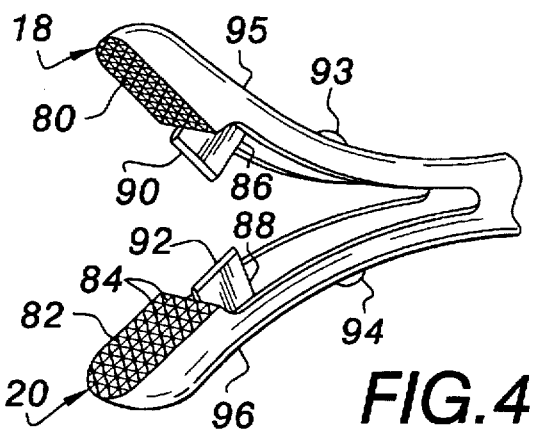
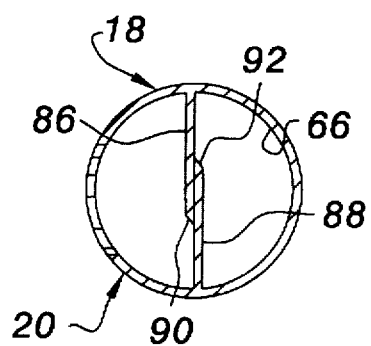
FIG.4   FIG.5
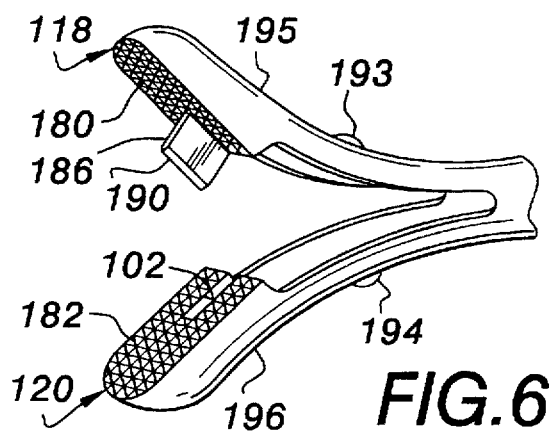
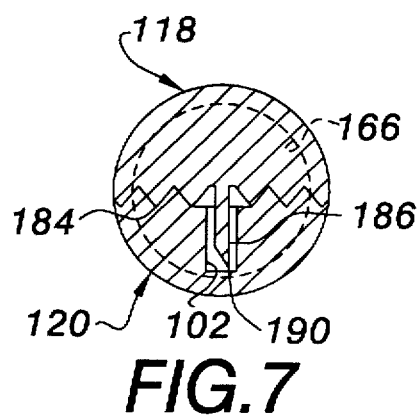
FIG.6   FIG.7
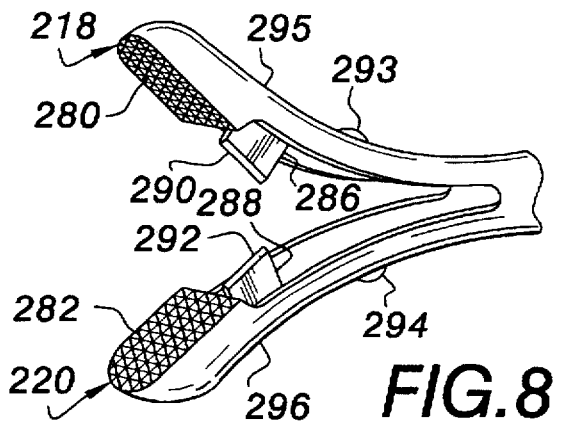
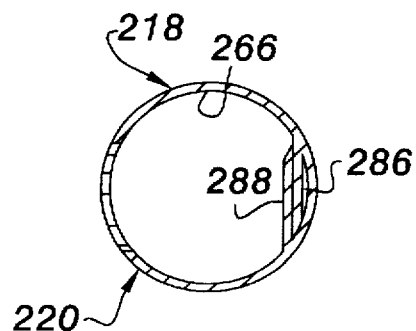
FIG.8   FIG.9
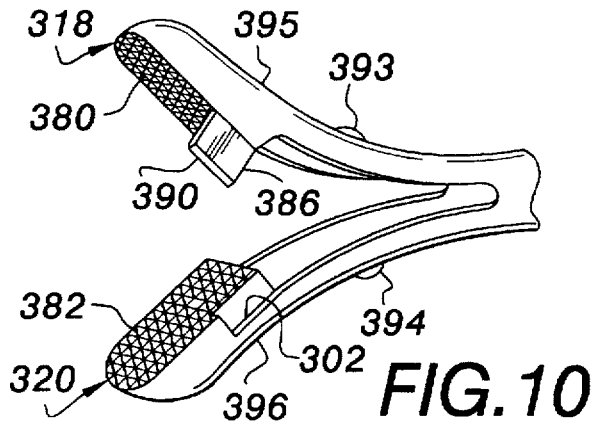
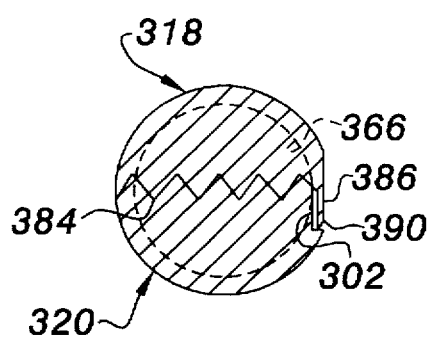
FIG.10   FIG.11

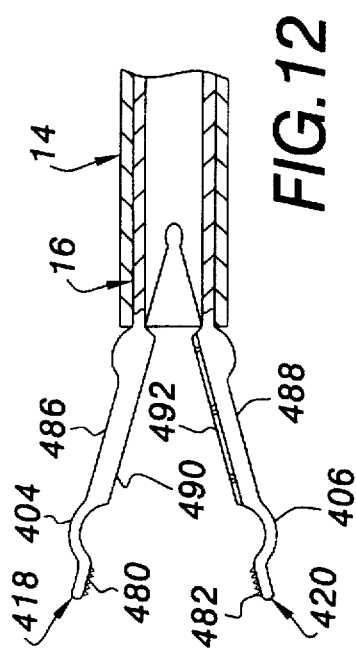
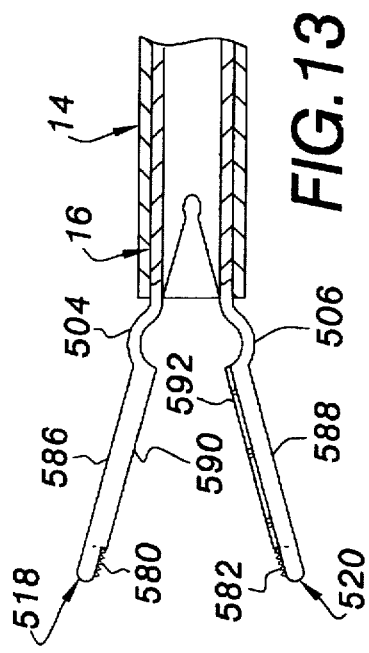
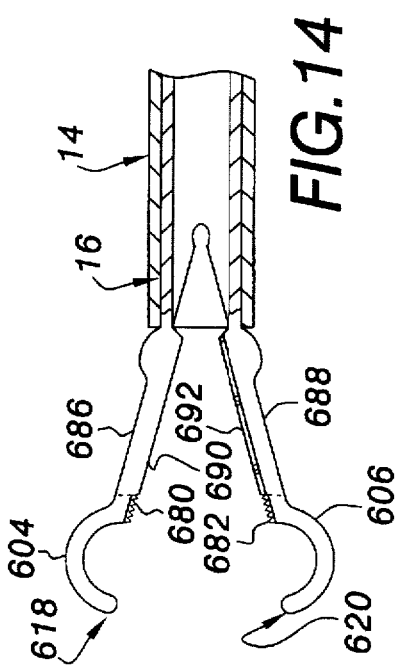
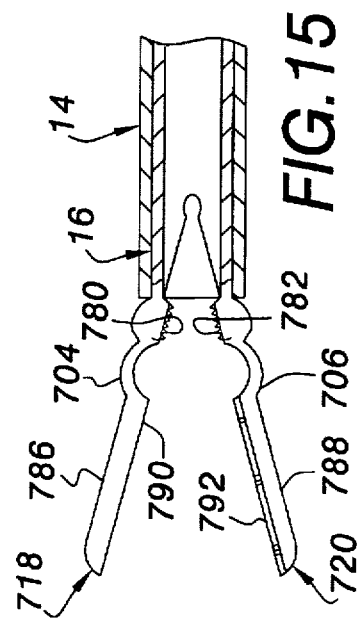
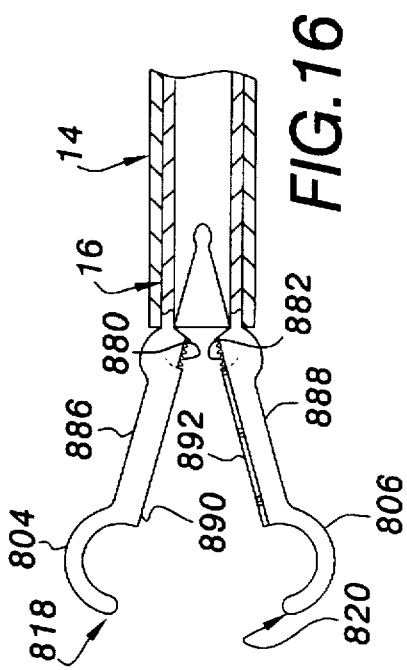
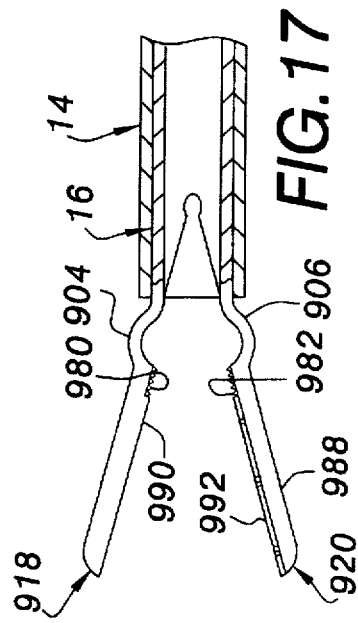

ENDOSCOPIC GRASPING INSTRUMENT WITH SCISSORS

CROSS-REFERENCE TO RELATED APPLICATIONS

This application is a continuation-in-part of applicant's patent applications Ser. No. 08/612,634, filed Mar. 6, 1996, pending and Ser. No. 08/376,186, filed Jan. 20, 1995, now U.S. Pat. No. 5,665,100, which are a continuation and a continuation-in-part, respectively, of patent application Ser. No. 08/281,814, filed Jul. 28, 1994, now abandoned, which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a division of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention

The present invention relates generally to medical procedures and instruments and, more particularly, to a multifunctional endoscopic grasping instrument with scissors.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, most endoscopic instruments are designed to perform only one of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming clean-up procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws increasing the risk of fluid leaking through poorly sealed pivotal mounts.

SUMMARY OF THE INVENTION

Accordingly, it is a primary object of the present invention to overcome the above-mentioned disadvantages of the prior art with an endoscopic instrument capable of performing multiple functions.

Another object of the present invention is to permit multiple functions to be performed with a single endoscopic instrument while defining a channel through the instrument for other instruments and/or fluids to be introduced at the operative site so that other functions can be performed without the need of having to remove the endoscopic instrument from the body.

Some of the advantages of the present invention over the prior art are that the endoscopic instrument can perform multiple functions through a single incision thereby minimizing the number of incisions required to perform an endoscopic procedure, that the frequency of substitution of instruments through a single incision can be reduced, that visualization of tissue through an operating channel formed through the instrument permits grasping and cutting operations to be performed with greater precision, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

These and other objects, advantages and benefits are realized with the present invention as generally characterized in an endoscopic instrument including a handle and an elongate tubular member having a proximal end coupled with the handle for being disposed externally of the anatomical cavity and a distal end for being disposed within the anatomical cavity and carrying a pair of opposed, relatively movable jaws. The jaws are operable by manipulation of the handle to perform multiple functions such as, for example, grasping objects such as needles and cutting tissue. In addition, the elongate tubular member defines a channel providing access to the operative site from outside the anatomical cavity without the need of having to remove the instrument from the cavity.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 4 is a fragmentary perspective view of the distal end of the endoscopic instrument of FIG. 1 with the jaws of the instrument in the open position.

FIG. 5 is a cross-sectional view of the instrument jaws taken through line 5—5 in FIG. 2.

FIG. 6 is a fragmentary perspective view of the distal end of a modification of the endoscopic instrument according to the present invention with the jaws of the instrument in an open position.

FIG. 7 is a cross-sectional view of the jaws of the endoscopic instrument of FIG. 6 in a closed position.

FIG. 8 is a fragmentary perspective view of the distal end of another modification of the endoscopic instrument according to the present invention with the jaws of the instrument in an open position.

FIG. 9 is a cross-sectional view of the jaws of the endoscopic instrument of FIG. 8 in a closed position.

FIG. 10 is a fragmentary perspective view of the distal end of yet another modification of the endoscopic instrument according to the present invention with the jaws of the instrument in an open position.

FIG. 11 is a cross-sectional view of the jaws of the endoscopic instrument of FIG. 10 in a closed position.

FIGS. 12–17 are fragmentary side views, partly in section, of further modifications of the instrument jaws according to the present invention.

DESCRIPTION OF THE PREFERRED EMBODIMENTS

The endoscopic instrument of the present invention can be utilized in any type of anatomical cavity; and, accordingly, while the instrument is described hereinafter for use with a portal sleeve in endoscopic procedures, such as laparoscopy, the instrument can be used with catheters and other small or large diameter tubular or hollow, cylindrical members providing access to small cavities, such as veins and arteries as well as large cavities, such as the abdomen.

Figure 1:
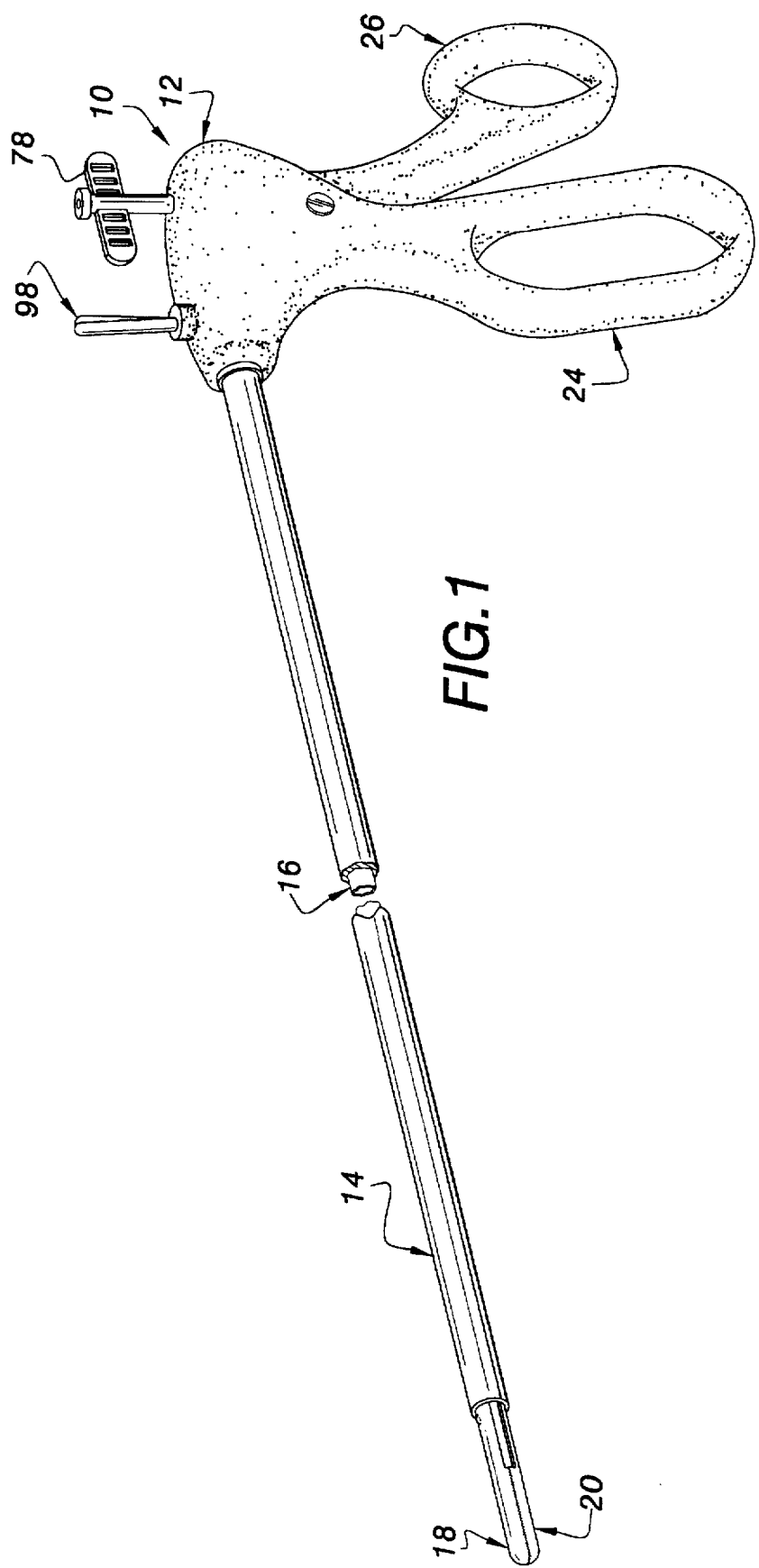
FIG. 1 is a perspective view, broken longitudinally, of an endoscopic instrument according to the present invention.
Figure 2:
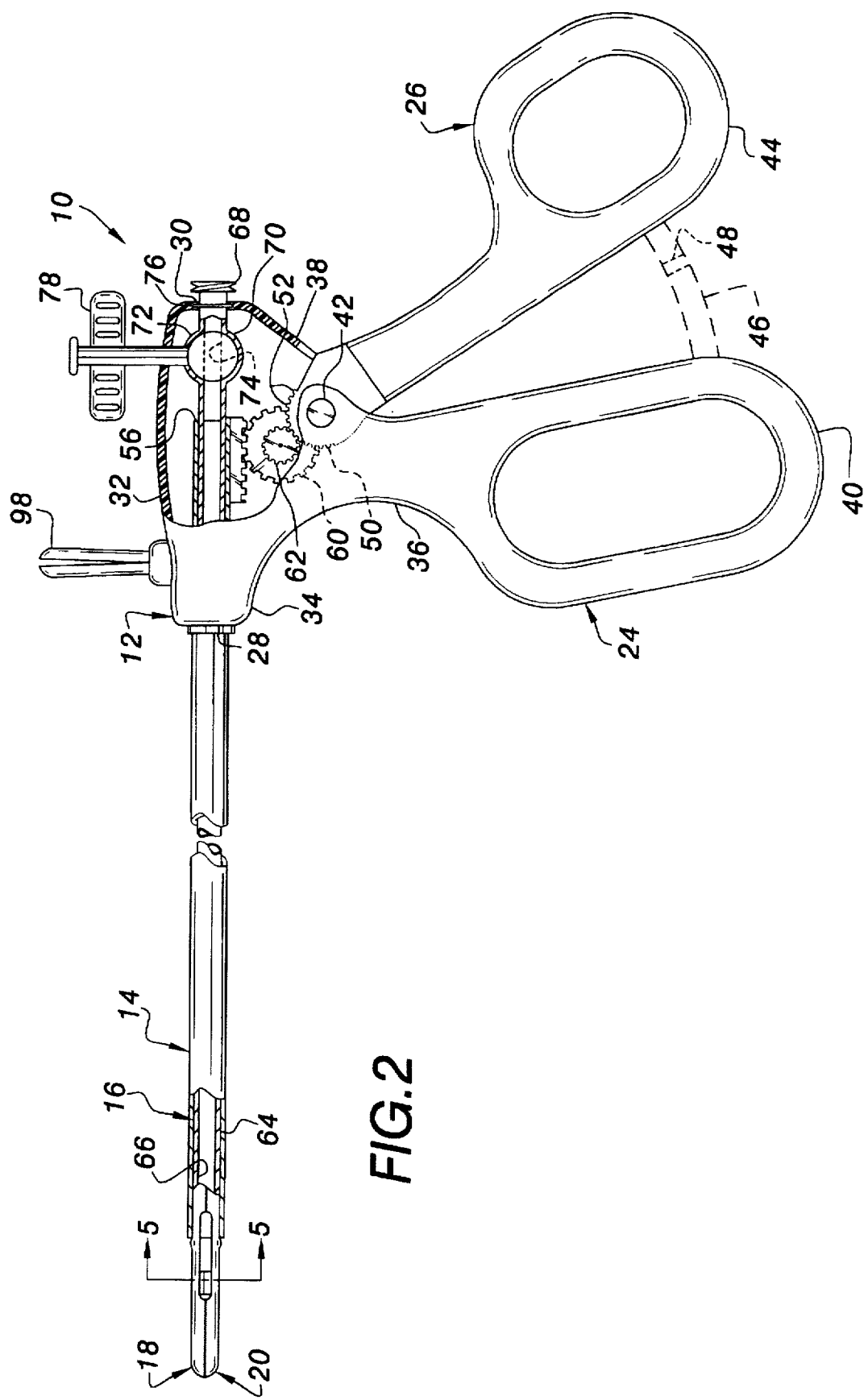
FIG. 2 is a broken side view, partly in section, of the endoscopic instrument of FIG. 1 with jaws of the instrument in a closed position.

An endoscopic instrument 10 in accordance with the present invention, as illustrated in FIGS. 1 and 2, includes a housing 12, an outer tubular member 14 extending distally from the housing 12, an inner tubular member 16 telescopically fitted within the outer tubular member and terminating distally in a pair of opposed jaws 18 and 20, and a handle portion formed of a fixed handle 24 and a movable handle 26.

Housing 12 includes longitudinally spaced front and rear walls 28 and 30 oriented perpendicular to a longitudinal axis of the instrument, a top wall 32 substantially parallel to the longitudinal axis and a bottom wall 34 having a concave forward portion 36 curving downwardly from the front wall to connect with an upper end of fixed handle 24 and a rearward portion 38 extending proximally at an angle relative to the longitudinal axis of the instrument from an upper end of the handle 24 to rear wall 30. A lower end of the fixed handle is configured as an elongate finger loop 40 to accommodate one or more fingers of a user. Movable handle 26 is pivotally mounted on a pin 42 proximally spaced from fixed handle 24 and secured internally to a wall or walls of the housing. A lower end of the handle 26 is configured as a finger loop 44 to accommodate one or more fingers of the user, and a pair of arcuate mating protrusions, shown by broken lines at 46 and 48 in FIG. 2, can optionally be carried in opposed relation on finger loops 40 and 44 for ratcheting engagement during operational use. Movable handle 26 includes an arcuate end portion 50 disposed within housing 12 and defining a plurality of gear teeth 52 on a side of pin 42 opposite finger loop 44.

Outer tubular member 14 is open at both ends and extends distally from housing 12 through an opening in the front wall 28 of the housing. Distal end 54 of outer tubular member 14 can be blunt as shown, tapered, beveled, slotted or chamfered as desired or have any other suitable distal configuration. Preferably, outer tubular member 14 is made of a cylindrical length of a substantially rigid material, such as stainless steel or other medically acceptable metal or plastic materials. The proximal end 56 of the outer tubular member is movably disposed within the housing and carries a rack 58 in spaced relation to the toothed end portion 50 of handle 26. A pinion gear 60 engages the rack 58 and is mounted on the same shaft as a reduction gear 62 which meshingly engages toothed end portion 50 of the handle to convert relatively small rotary or pivotal movement of the handle into significantly larger linear movement of the rack. Looking at FIGS. 2 and 3, it will be appreciated that counterclockwise rotation of handle 26 about pin 42 results in proximal movement of outer tubular member 14 relative to housing 12 and that clockwise rotation of handle 26 about pin 42 results in distal movement of outer tubular member 14 relative to housing 12. In a preferred embodiment, movable handle 26 is biased in a clockwise direction toward fixed handle 24, for example by use of a torsion spring (not shown) coiled around pin 42 and connected between the movable handle and the fixed handle and/or the housing.

Figure 3:
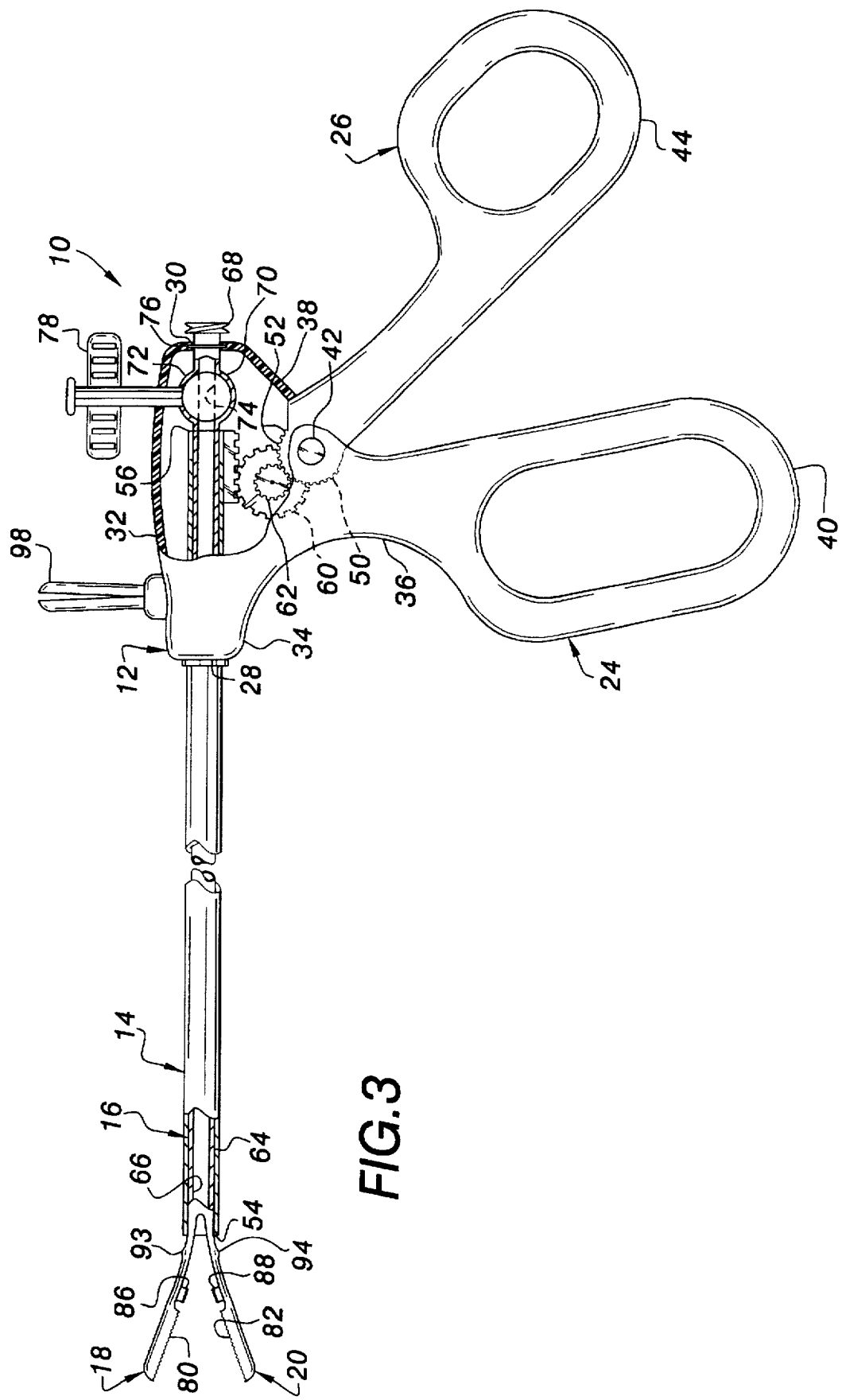
FIG. 3 is a broken side view, partly in section, of the endoscopic instrument of FIG. 1 with the jaws of the instrument in an open position.

Inner member 16 includes a tubular portion 64 telescopically fitted within outer tubular member 14 and defining a lumen or channel 66 through the instrument. The proximal end of the inner member extends through the rear wall of housing 12 and terminates at a coupling 68, for example a Luer lock, for connection with sources of fluid or suction, other medical instruments and operating units such as those shown and described in my pending application Ser. No. 08/376,186, the disclosure of which has been incorporated herein by reference. A hollow, spherically-shaped valve housing 70 is distally spaced from the coupling within the housing, and a spherical valve member 72 having a cylindrical aperture or passage 74 formed therethrough is rotatably disposed within the valve housing and connected with a knob 78 extending upwardly through an opening in the top wall of the housing to permit manual operation of the valve from outside the housing. The inner member is fixed relative to the housing with a flange 76 mounted between the coupling and the valve and received within a slotted recess formed in rear wall 30. The distal end of tubular portion 64 is bifurcated or split longitudinally to form integral one-piece jaws 18 and 20 in opposed relation, the jaws being normally biased apart as shown in FIGS. 3 and 4. Referring to FIG. 4, in particular, jaws 18 and 20 cooperate to define a grasping portion at a distal end having opposed inner surfaces 80 and 82 formed with conventional diamond-shaped protrusions or teeth 84 for securely holding a suture needle, anatomical tissue or any other useful object when closed and a cutting portion proximally spaced from the grasping portion and including a pair of cutting members or blades 86 and 88 carried by the jaws in opposed relation. As best seen in FIGS. 4 and 5, blades 86 and 88 are proximally spaced from grasping surfaces 80 and 82 and are mounted to project inwardly along a central longitudinal axis of each jaw in generally opposed relation so that sharp tissue cutting edges 90 and 92 of the blades slidingly engage one another like a scissors when the jaws are moved between the closed position or condition shown in FIG. 2 and the open position or condition shown in FIG. 3. The blades are shown oriented parallel to a longitudinal axis of the inner tubular member but can be oriented at any angle relative to the longitudinal axis dependent upon procedural use. Wedge-like cams 93 and 94 protrude outwardly from respective outer surfaces 95 and 96 of jaws 18 and 20 and taper inwardly in the proximal direction to present an angled cam surface against which the distal end of outer tubular member 14 can act to force the jaws together.

Tubular body 64 of the intermediate member is preferably formed with jaws 18 and 20 as a single unitary part using a resilient medically-acceptable material such as, for example, a spring steel or a plastic material having suitable elastic properties for normally biasing the upper and lower jaws apart while permitting the jaws to be moved toward one another in response to forces acting on the outer jaw surfaces and/or cams as a result of relative axial movement between the outer tubular member and the inner member. Blades 86 and 88 can be formed integrally with the jaws as a one-piece unit or formed separately of the jaws and connected thereto in any suitable manner such as, for example, by adhesive bonding, welding or mechanical attachment. Preferably, the blades are formed of a medical grade metal material such as stainless steel or titanium.

An insulated connector 98 can optionally be mounted on housing 12 opposite the handle portion or anywhere else on the instrument to connect with electrically conductive elements of the instrument for performing unipolar or bipolar electric coagulation, for example using one or both of the blades as conductive elements.

In use, instrument 10 is grasped using finger loops 40 and 44 and is guided to the operative site via a portal sleeve positioned in the wall of an anatomical cavity. The portal sleeve can be positioned in the anatomical cavity wall using any suitable penetrating technique, including those creating puncture sites by means of removable obturators such as trocars, and can include a valve housing, if desired, to prevent loss of pneumoperitoneum during insertion and withdrawal of the instrument. Visualization of the endoscopic procedure can be accomplished using a conventional endoscope incorporated into the instrument, for example within the central channel 66 defined by tubular shaft 64, or separately positioned within the anatomical cavity through a second portal sleeve located at another puncture site.

Instrument 10 is advanced distally through the portal sleeve until jaws 18 and 20 emerge into the anatomical cavity. At this point, the instrument can be manipulated externally of the body to position the jaws at the operative site. Various grasping and cutting functions can be performed at the operative site using different portions of the jaws and by operating the handles of the instrument to open and close the jaws as required. Since inner member 16 is fixed relative to housing 12, actuation of the jaws to open or close is controlled by moving outer tubular member 14 relative to the inner member. If closed, jaws 18 and 20 can be opened by moving outer tubular member 14 proximally relative to inner member 16. Movement of the outer tubular member over the inner member is controlled by operation of movable handle 26. Counterclockwise rotation of handle 26 about pin 42 results in clockwise rotation of reduction gear 62 which, in turn, causes an equal angular rotation of pinion 60. Pinion 60 is of greater diameter than reduction gear 62 so that, for equal angles of rotation, pinion 60 will produce greater circumferential displacement. Pinion 60 engages the gear teeth of rack 58 to cause proximal movement of the outer tubular member 14 relative to jaws 18 and 20 thereby permitting the jaws to move resiliently to the open position shown in FIG. 3. In the open position, jaws 18 and 20 are biased apart such that inner surfaces 80 and 82 of the jaws and cutting edges 90 and 92 of the blades are angularly spaced from one another allowing objects to be positioned between different portions of the jaws. Conversely, clockwise rotation of the handle 26 about pin 42 results in counterclockwise rotation of reduction gear 62 and pinion 60 causing distal movement of rack 58 and outer tubular member 14 relative to the jaws so that distal end 54 of the outer tubular member will slide over the jaws in an axial direction causing the jaws to be cammed inwardly from the open position to the closed position. As the jaws move from the open position to the closed position, inner surfaces 80 and 82 will rotate toward another to grasp objects, such as needles or tissue, disposed therebetween, and cutting edges 90 and 92 of the blades will slidingly engage one another like a scissors to cut objects, such as tissue or unsecured lengths of suture material, placed between the blades when the jaws are in the open position.

Movable handle 26 is preferably proximally spaced from fixed handle 24 as shown so that the user can maintain one or more fingers on the stationary handle 24 while operating the movable handle 26 with the thumb and/or other fingers of the hand. Movable handle 26 is preferably biased in a clockwise direction, looking at FIG. 3, toward stationary handle 24 so that, when the movable handle is released, outer tubular member 14 will be automatically moved over jaws 18 and 20 to close the jaws together, for example to hold a suture needle between the jaws during complicated maneuvers requiring free hand movement.

In addition to performing various grasping and cutting functions, the endoscopic instrument 10 permits access to the operative site from outside the body through channel 66 formed through the instrument between proximal and distal ends of the inner tubular member. The channel can, for example, be used to introduce lengths of suture material (with or without knotting elements attached thereto) as well as any other medical devices or instruments, such as endoscopes or probes, or to perform irrigation or aspiration at the operative site, for example by attaching a source of fluid or suction to the coupling at the proximal end of the inner member, or to administer medicaments as desired.

FIGS. 6 and 7 illustrate a modification of the jaws of the endoscopic instrument according to the present invention wherein the modified upper jaw 118 carries a blade 186 with a cutting edge 190 and the modified lower jaw 120 defines a concave recess or pocket 102 for receiving the blade. Blade 186 extends perpendicularly from a proximal end of inner surface 180 of the needle holding portion of the upper jaw and is centrally located along the longitudinal axis of the inner member in opposed relation to the pocket, which is formed in the proximal end of inner surface 182 of the needle holding portion of the lower jaw. Cutting edge 190 of the blade is angularly spaced from the lower jaw when the jaws are in the open position as shown in FIG. 6, permitting anatomical tissue and other objects to be positioned between the blade and the pocket. When jaws 118 and 120 are closed, blade 186 moves toward pocket 102 and is received therein to cut any object held between the cutting portion of the jaws. As seen in FIG. 7, jaws 118 and 120 can be closed completely when blade 186 is disposed within pocket 102 and can thus compress or flatten the tissue or object held therebetween if desired.

The modified jaws 218 and 220 shown in FIGS. 8 and 9 are similar to the jaws described above but carry a pair of blades 286 and 288 disposed proximally of inner grasping surfaces 280 and 282 in opposed relation along lateral edges of the jaws. Blades 286 and 288 depend perpendicularly from opposed lateral edges of the jaws and have opposed cutting edges 290 and 292 spaced apart when jaws 218 and 220 are open to permit positioning of anatomical tissue and other objects between the blades. When jaws 218 and 220 are closed, cutting edges 290 and 292 of the blades move towards one another and into sliding contact to cut any tissue or objects held between the jaws. As best seen in FIG. 9, the off-axis or eccentric position of the blades also facilitates visualization of the procedure through an endoscopic instrument positioned within channel 266.

FIGS. 10 and 11 illustrate a further modification of the endoscopic instrument wherein the upper jaw 318 carries an off-axis or eccentric blade 386 with cutting edge 390 and the lower jaw 320 defines a concave pocket 302 for receiving the blade. Blade 386 extends perpendicularly from a proximal end of inner grasping surface 380 of the needle holding portion of the upper jaw and is laterally spaced from the central longitudinal axis of the inner member to be disposed along an outer peripheral edge of the jaw in opposed relation to pocket 302. Cutting edge 390 of the blade is angularly spaced from pocket 302 in lower jaw 320 when the jaws are open permitting anatomical tissue and other objects to be positioned between the blade and the pocket. When jaws 318 and 320 are closed, blade 386 moves toward pocket 302 and is received therein to cut any tissue or object held between the jaws.

The grasping portion of the instrument jaws can be suitably configured to grasp any type of object during an endoscopic procedure. As described above, the grasping portion can be configured to include opposed surfaces which are caused to meet or come very close to one another to clamp objects such as needles positioned between the jaws by exerting a compressive force on the objects as the jaws are moved toward one another. Under certain circumstances, however, medical personnel may wish to hold an object without deforming or compressing the object, for example when moving or manipulating certain tubular organs. FIGS. 12–17 illustrate modifications of the endoscopic instrument wherein the jaws are provided with concave holding portions between which objects may be held without being deformed or compressed. In FIG. 12, the modified upper and lower jaws 418 and 420 include grasping surfaces 480 and 482 disposed distally of cutting members 486 and 488, respectively, and concave portions 404 and 406 of arcuate configuration disposed between the grasping surfaces and the cutting members and facing one another in opposed relation to define a circular or other suitably shaped opening therebetween when the jaws are closed, the opening having a size and shape to surround selected objects, such as tubular vessels and organs, without substantially traumatically compressing the objects. The modified instrument jaws 518 and 520 shown in FIG. 13 are similar to those shown in FIG. 12 but with concave portions 504 and 506 disposed proximally of grasping surfaces 580 and 582, and cutting members 586 and 588 disposed between the concave portions and the grasping surfaces. Another modification of the instrument jaws is shown in FIG. 14 wherein upper and lower jaws 618 and 620 are similar to those described above but with concave portions 604 and 606 disposed distally of cutting members 686 and 688, and grasping surfaces 680 and 682 disposed between the concave portions and the cutting members. In the modification of the instrument jaws shown in FIG. 15, upper and lower jaws 718 and 720 are similar to those described above but with grasping surfaces 780 and 782 disposed proximally of cutting members 786 and 788, and concave portions 704 and 706 disposed between the grasping surfaces and the cutting members. The modified instrument jaws 818 and 820 shown in FIG. 16 are similar to those described above but with concave portions 804 and 806 disposed distally of grasping surfaces 880 and 882, and cutting members 886 and 888 disposed between the concave portions and the grasping surfaces. Yet another modification of the instrument jaws is shown in FIG. 17 wherein upper and lower jaws 918 and 920 are similar to those described above but with concave portions 904 and 906 disposed proximally of cutting members 986 and 988, and grasping surfaces 980 and 982 disposed between the concave portions and the cutting members.

From the above, it will be appreciated that the endoscopic instrument according to the present invention permits multiple grasping and cutting functions to be performed with a single instrument while defining a channel for fluids and other medical instruments and probes to be introduced at the operative site without the need of having to remove the endoscopic needle-holding instrument from the body.

The jaws making up the jaw portion of the endoscopic instrument can be formed as an integral one-piece unit or assembled from separate pieces; and, depending on procedural use, one of the jaws can be fixed and the other movable, both jaws can be movable, the jaws can be linked by pivots or formed at the end of a tubular member or formed at the end of a pair of pivotally connected arms. The jaws, including any of the grasping or cutting portions thereof, can be straight, curved and/or angled as desired. Any of the jaws shown or described herein can be formed with opposed inner surfaces formed of repeated patterns of diamond-shaped protrusions, lateral and/or longitudinal ribs and/or other types of structural features suitable for holding needles and other types of objects during an endoscopic procedure. The jaws can have any shape in transverse cross-section when closed including, but not limited to, circular, elliptical, rectangular and polygonal configurations, and can have opposed arcuate or concave portions for holding objects, such as tubular organs, without traumatically compressing the objects. The jaws can also be of varying width in the longitudinal direction such that, for example, relatively thin cutting members or blades can be formed along a first longitudinal portion of the jaws and grasping portions of greater width than the cutting members can be formed at longitudinally spaced locations relative to the cutting members.

The cutting members or blades can be carried by one or both jaws and centrally located for cutting anatomical tissue, unsecured lengths of suture material or any other objects normally cut during a surgical procedure, or the blades can be offset laterally from the central longitudinal axis of the jaws to permit better visualization and to allow the formation of longitudinal grooves or openings through the jaws when closed. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together. Furthermore, the blades can have straight, curved or angled cutting edges and can be oriented at any angle relative to a longitudinal axis of the jaws.

The handle portion of the endoscopic instrument shown and described herein is exemplary of the types of conventional handle mechanisms suitable for performing the function of actuating the jaws; accordingly, the handles can have any configuration to actuate the jaws including, but not limited to, configurations employing a pair of pivotally connected arms, one fixed and one pivoted arm, a pistol grip with a movable trigger, or resilient U-shaped handle members. Further, the handle portion of the instrument can be configured to rotate relative to a pivot axis oriented perpendicular to the longitudinal axis of the instrument so that, for example, in one position the handles will extend laterally from the instrument or at a substantially perpendicular angle relative to the longitudinal axis; while, in another position, the handles will extend proximally from the instrument like scissor handles.

It will be appreciated that the handle portion and jaw portion of the endoscopic instrument can be integrally formed as a one-piece unit or formed as separate components and coupled together, for example, by use of pivots, linkages, rods, cables, telescoping members, brackets and other mechanical and/or electrical couplings.

When the instrument is formed of telescoping members, it will also be appreciated that individual tubular members, such as the inner member can be made rotatable about a longitudinal axis of the instrument either alone or in combination with other telescoping members. Moreover, when the instrument is coupled with a source of fluid or suction, an operating unit or other medical device, the instrument housing can have any configuration for being releasably coupled including, but not limited to threaded or telescoping portions, detents, latches or any other suitable connections. Furthermore, the housing can be cylindrical or rectangular or have any other useful or convenient configuration in cross-section.

The inner member can define one channel as shown or multiple channels of similar or different cross-sectional configuration. Any of the channels defined by the inner member can be coaxially disposed or offset from the central longitudinal axis of the inner member and can have any suitable configuration in cross-section dependent upon procedural use including, but not limited to, circular, elliptical and polygonal cross-sectional configurations.

The outer tubular member can have any suitable configuration in cross-section to fit through a portal formed in the wall of an anatomical cavity and to receive the inner member for sliding movement therein. The distal end of the outer tubular member can be blunt, tapered, beveled or chamfered, and can also be provided with longitudinal slots or interior grooves for receiving protrusions or cams carried on the outer surfaces of the jaws to assist in maintaining proper alignment of the jaw blades when cutting tough materials. Alternatively, protrusions can be carried on an interior surface of the outer tubular member in alignment with slots or grooves formed in the jaws to maintain alignment during operational use.

The components of the endoscopic instrument of the present invention can be made of any suitable, medical grade materials to permit sterilization for reuse or disposal for single patient use. The components can be made of multiple parts of various configurations and materials to reduce cost and/or simplify fabrication. The instrument can have various valves, stop cocks and seals in the housing and/or inner member to control fluid flow therethrough.

The features of the various embodiments described above can be combined in any manner desired dependent upon the operational requirements of the procedure to be performed and the complexity of the endoscopic instrument.

Inasmuch as the present invention is subject to many variations, modifications and changes to detail it is intended that all subject matter discussed above or shown in the accompanying drawings be interpreted as illustrative only and not be taken in a limiting sense.

What is claimed is:

1. A multifunctional endoscopic instrument for use in performing endoscopic procedures within an anatomical cavity comprising a handle; and an elongate tubular member having a proximal end coupled with said handle for being disposed externally of the anatomical cavity and a distal end for being disposed within the anatomical cavity and carrying a pair of opposed, relatively movable jaws;

said jaws defining a grasping portion operable by manipulation of said handle to grasp objects and a cutting portion operable by manipulation of said handle to cut tissue.

2. A multifunctional endoscopic instrument for use in performing endoscopic procedures within an anatomical cavity as recited in claim 1 wherein said tissue cutting portion includes a blade.

3. A multifunctional endoscopic instrument for use in performing endoscopic procedures within an anatomical cavity as recited in claim 1 wherein said tissue cutting portion includes a pair of blades carried by said jaws in opposed relation.

4. A multifunctional endoscopic instrument for use in performing endoscopic procedures within an anatomical cavity as recited in claim 1 wherein said tissue cutting portion includes a blade carried by a first of said jaws and a recess formed in a second of said jaws in opposed relation to said blade to receive said blade when said jaws are moved toward one another.

5. A multifunctional endoscopic instrument for use in performing endoscopic procedures within an anatomical cavity as recited in claim 2 wherein said blade is oriented parallel to a longitudinal axis of said elongate tubular member.

6. A multifunctional endoscopic instrument for use in performing endoscopic procedures within an anatomical cavity as recited in claim 5 wherein said blade is disposed along a central longitudinal axis of said elongate tubular member.

7. A multifunctional endoscopic instrument for use in performing endoscopic procedures within an anatomical cavity as recited in claim 5 wherein said blade is laterally offset from a central longitudinal axis of said elongate tubular member.

8. A multifunctional endoscopic instrument for use in performing endoscopic procedures within an anatomical cavity as recited in claim 1 wherein said grasping portion is longitudinally spaced from said tissue cutting portion to hold a needle.

9. A multifunctional endoscopic instrument for use in performing endoscopic procedures within an anatomical cavity as recited in claim 1 wherein said jaws include opposed concave portions longitudinally spaced from said tissue cutting portion for defining an opening between said jaws to hold an object during an endoscopic procedure without compressing the object.

10. A multifunctional endoscopic instrument for use in performing endoscopic procedures within an anatomical cavity as recited in claim 1 wherein said grasping portion is disposed distally of said cutting portion and wherein at least one of said jaws includes a concave portion between said grasping portion and said tissue cutting portion to hold an object during an endoscopic procedure without compressing the object.

11. A multifunctional endoscopic instrument for use in performing endoscopic procedures within an anatomical cavity as recited in claim 1 wherein at least one of said jaws includes a concave portion distally spaced from said tissue cutting portion to hold an object during an endoscopic procedure without compressing the object and wherein said grasping portion is disposed between said concave portion and said tissue cutting portion.

12. A multifunctional endoscopic instrument for use in performing endoscopic procedures within an anatomical cavity as recited in claim 1 wherein said grasping portion is disposed distally of said tissue cutting portion and at least one of said jaws includes a concave portion proximally spaced from said tissue cutting portion to hold an object during an endoscopic procedure without compressing the object.

13. A multifunctional endoscopic instrument for use in performing endoscopic procedures within an anatomical cavity as recited in claim 1 wherein said grasping portion is proximally spaced from said tissue cutting portion and at least one of said jaws includes a concave portion distally spaced from said tissue cutting member to hold an object during an endoscopic procedure without compressing the object.

14. A multifunctional endoscopic instrument for use in performing endoscopic procedures within an anatomical cavity as recited in claim 1 wherein said grasping portion is proximally spaced from said tissue cutting portion and at least one of said jaws includes a concave portion disposed between said grasping portion and said tissue cutting portion to hold an object during an endoscopic procedure without compressing the object.

15. A multifunctional endoscopic instrument for use in performing endoscopic procedures within an anatomical cavity as recited in claim 1 wherein at least one of said jaws includes a concave portion proximally spaced from said tissue cutting portion to hold an object during an endoscopic procedure without compressing the object and wherein said grasping portion is disposed between said concave portion and said tissue cutting portion.

16. A multifunctional endoscopic instrument for use in performing endoscopic procedures within an anatomical cavity as recited in claim 1 wherein said proximal and distal ends of said elongate tubular member are open and further comprising a valve disposed between said proximal and distal ends.

17. A multifunctional endoscopic instrument for use in performing endoscopic procedures within an anatomical cavity as recited in claim 1 and further comprising a coupling carried at said proximal end of said elongate tubular member for connection with other medical instruments.

18. A multifunctional endoscopic instrument for use in performing endoscopic procedures within an anatomical cavity as recited in claim 1 wherein said jaws are biased apart toward an open position and further comprising an outer tubular member disposed telescopically around said elongate tubular member and having a proximal end coupled with said handle and a distal end movable relative to said elongate tubular member by manipulation of said handle between a retracted position allowing said jaws to open and an extended position causing said jaws to close.

* * * * *